United States Patent [19]
Marlin

[11] Patent Number: 5,917,076
[45] Date of Patent: Jun. 29, 1999

[54] PROCESS FOR THE PREPARATION OF SPIRO BIS-PHOSPHITES USING FINELY GROUND PENTAERYTHRITOL

[75] Inventor: Gary Marlin, Morgantown, W. Va.

[73] Assignee: General Electric Company, Pittsfield, Mass.

[21] Appl. No.: 09/061,292

[22] Filed: Apr. 16, 1998

[51] Int. Cl.⁶ .................................................. C07F 9/6574
[52] U.S. Cl. .............................................................. 558/78
[58] Field of Search ................................................. 558/78

[56] References Cited

U.S. PATENT DOCUMENTS

| | | |
|---|---|---|
| 3,039,993 | 6/1962 | Friedman . |
| 3,056,823 | 10/1962 | Hechenbleikner . |
| 3,281,381 | 10/1966 | Hechenbleikner . |
| 3,281,506 | 10/1966 | Shepard et al. . |
| 3,305,526 | 2/1967 | Guttag . |
| 3,342,767 | 9/1967 | Buckley . |
| 3,415,906 | 12/1968 | Shepard et al. . |
| 3,441,633 | 4/1969 | Friedman . |
| 3,467,733 | 9/1969 | Dever . |
| 3,482,002 | 12/1969 | Dever . |
| 3,488,407 | 1/1970 | Schall . |
| 3,558,554 | 1/1971 | Kurlyama . |
| 3,845,168 | 10/1974 | Guttag . |
| 4,024,049 | 5/1977 | Shell et al. . |
| 4,067,903 | 1/1978 | Hoch et al. . |
| 4,086,304 | 4/1978 | Hutton et al. . |
| 4,196,117 | 4/1980 | Spivack . |
| 4,237,075 | 12/1980 | Gough . |
| 4,276,233 | 6/1981 | Markezich et al. . |
| 4,312,818 | 1/1982 | Maul et al. . |
| 4,318,845 | 3/1982 | Spivack et al. . |
| 4,322,530 | 3/1982 | Jachimowicz . |
| 4,371,647 | 2/1983 | Minagawa et al. . |
| 4,391,761 | 7/1983 | Block et al. . |
| 4,407,765 | 10/1983 | Hardy . |
| 4,440,696 | 4/1984 | Maul et al. . |
| 4,492,661 | 1/1985 | Maul et al. . |
| 4,656,302 | 4/1987 | Dressler . |
| 4,705,879 | 11/1987 | Dressler . |
| 4,724,056 | 2/1988 | Doane . |
| 4,786,329 | 11/1988 | Chang et al. . |
| 4,882,374 | 11/1989 | Wang et al. . |
| 4,894,481 | 1/1990 | Burt . |
| 5,126,475 | 6/1992 | Bahrmann et al. . |
| 5,141,975 | 8/1992 | Enlow . |
| 5,235,086 | 8/1993 | Maul et al. . |
| 5,254,709 | 10/1993 | Hunter . |
| 5,371,263 | 12/1994 | Quotschalla et al. . |
| 5,424,348 | 6/1995 | Mahood . |
| 5,438,086 | 8/1995 | Stevenson et al. . |
| 5,468,895 | 11/1995 | Mahood . |
| 5,534,645 | 7/1996 | Quotschalla et al. . |

Primary Examiner—Michael G. Ambrose

[57] ABSTRACT

A process for producing organo-phosphites of the formula

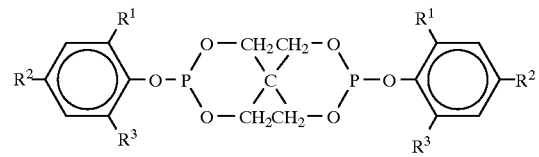

wherein $R^1$ and $R^2$ are each 2,4-di-tert-butyl and $R^3$ is hydrogen is provided. The process involves heating a reaction mixture containing pentaerythritol wherein the pentaerythritol has an average particle size of about 250 microns or less, preferably the pentaerythritol has an average particle size of about 150 microns or less, phosphorous trihalide, a phenolic compound of the formula:

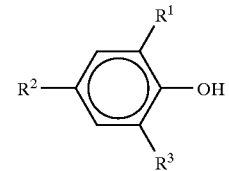

wherein each $R^1$ and $R^2$ is t-butyl and $R^3$ is hydrogen, a solvent selected from the group consisting of heptane, hexane, octane, xylene, toluene, and mixtures of the solvents containing at least one of the aforementioned and a catalyst. The process utilizing the aforementioned pentaerythritol particle size has the unexpected advantages of short reaction times as compared to the same process using a larger pentaerythritol particle size.

24 Claims, No Drawings

PROCESS FOR THE PREPARATION OF SPIRO BIS-PHOSPHITES USING FINELY GROUND PENTAERYTHRITOL

FIELD OF THE INVENTION

This invention relates to a process for the preparation of organic phosphites, specifically spiro bis-phosphites. In an especially preferred embodiment, this invention relates to a process to prepare bis(dialkylphenyl)pentaerythritol diphosphites from finely ground pentaerythritol, dialkyl-substituted phenol, and a phosphorous trihalide.

BACKGROUND OF THE INVENTION

Organic phosphites are used in the stabilization of a wide variety of polymeric systems. Many different phosphites have been proposed for use either alone or in combination with other stabilizers. Such phosphites and their utilities are described in U.S. Pat. Nos. 4,371,647, 4,656,302, 4,705,879, 5,126,475, 5,141,975, and 5,438,086. The importance of organic phosphites as stabilizers has lead to the development of a variety of specialty organic phosphites that have enhanced effectiveness for stabilization.

Sterically hindered organic phosphites, and in particular diphosphites based upon pentaerythritol and containing alkyl, aryl, or alkyl-substituted aryl groups wherein the substitution is selected from the group consisting of t-butyl, t-amyl, t-hexyl, cyclohexyl, t-pentyl, and t-octyl, are especially desirable compounds due to their enhanced hydrolytic stability, ease of handling and compatibility with a wide variety of polymeric systems. The bis(2,4-di-tertbutylphenyl)pentaerythritol diphosphites are also especially preferred for their improved hydrolytic stability over other alkyl substituted phosphites as well as their enhanced compatibility with some polymeric resins, especially polyolefins.

The organic diphosphites are generally prepared using methods involving reactions between the appropriate hydroxy compounds and phosphorous trihalides, e.g., phosphorous trichloride. Such methods and other useful methods are described in U.S. Pat. Nos. 3,839,506, 4,116,926, 4,290,976, 4,440,696, and 4,492,661. The ease of substitution of the halides on the phosphorous trihalide decreases as each halide is replaced. For example, in the preparation of bis (aryl)pentaerithritol diphosphites, the pentaerithritol hydroxyls readily react with a phosphorous trihalide to yield a bis(disubstituted halo phosphite (i.e., an intermediate di-substituted diphosphorohalidite). The displacement of the third halo group is less than quantitative and is considerably slower in rate. Additionally, displacement of the third halo group by a sterically hindered phenol is even more difficult and requires elevated temperatures and/or use of a catalyst.

In order to increase the rate of reaction and the degree of completion for displacing the third halide with a sterically hindered moiety, various techniques have been generally utilized in the art. These techniques include: elevating the reaction mixture temperature and the use of hydrogen halide acceptors, e.g., amines. Such techniques are described in U.S. Pat. Nos. 3,281,506, 4,237,075, 4,312,818, 4,440,696, and 4,894,481.

Generally in the case of diphosphites derived from pentaerythritol, the procedures of the prior art result in undesirable product mixtures including caged structures wherein three of the hydroxyls on a single pentaerythritol have reacted with one phosphorous trihalide. Additionally, various polyphosphite compounds are also formed leading to low conversions to the desired product. The resulting phosphite mixture containing a halo-phosphite is extremely difficult to purify and the residual halo-phosphite can lead to acid impurities that affect the long term stability of the desired organic phosphite.

Various processes have been described in the prior art yet each suffers from some undesirable limitation. For example, U.S. Pat. No. 4,739,090 describes a process utilizing xylene as a solvent. The final product is isolated by filtration and the filtrate can be recycled. This process is deficient in resulting in at least about five percent or more impurities that require further crystallization to remove. This patent is silent on the form of the pentaerythritol utilized in the reaction.

U.S. Pat. No. 5,103,035 describes low temperature reaction conditions in chlorinated solvents. This process is undesirable due the difficulties in safely handling chlorinated solvents and a second solvent has to be utilized in order to bring the final product out of solution.

U.S. Pat. No. 5,438,086 describes a process for making diphosphites based upon pentaerythritol and 2,4-dicumylphenol wherein the dicumyl phenol is first reacted with phosphorous trichloride followed by allowing the reaction with the pentaerythritol. This process afforded only a 66% yield and acid numbers of 2 to 6, both of which are unacceptable.

It is therefore apparent that a need continues to exist for improved processes for the preparation of bis(dialkylphenyl) pentaerythritol diphosphites, and especially bis(2,4-di-tertbutylphenyl)pentaerythritol diphosphite, that overcome the aforementioned difficulties.

SUMMARY OF THE INVENTION

The present invention relates to a new process for the production of organic spiro bis-phosphites from pentaerythritol, phosphorous trihalide, and a hydroxyl-containing compound, preferably a sterically hindered phenol, wherein the pentaerythritol has an average particle size of about 250 microns or less.

In a first embodiment of the present invention, the pentaerythritol, phosphorous trihalide, and a hydroxyl-containing compound are allowed to react together in a hydrocarbon solvent, wherein the pentaerythritol has an average particle size of about 250 microns or less.

In a second embodiment of the present invention, the pentaerythritol, phosphorous trihalide, and a hydroxyl-containing compound are allowed to react together in a hydrocarbon solvent in the presence of a catalyst, wherein the pentaerythritol has an average, particle size of about 250 microns or less.

In a third embodiment of the present invention, the pentaerythritol, phosphorous trihalide, and a hydroxyl-containing compound are allowed to react together in a hydrocarbon solvent in the presence of an amine catalyst, wherein the pentaerythritol has an average particle size of about 250 microns or less, and wherein the amine catalyst is capable of forming an amine hydrochloride salt that is soluble in the hydrocarbon solvent.

In a fourth embodiment of the present invention, the pentaerythritol, phosphorous trihalide, and a hydroxyl-containing compound are allowed to react together in a hydrocarbon solvent, wherein the pentaerythritol has an average particle size of about 250 microns or less, and the reaction temperature is maintained at less than about 90° C. until the pentaerythritol has been consumed.

In a fifth embodiment of the present invention, the pentaerythritol, phosphorous trihalide, and a hydroxyl-containing compound are allowed to react in a hydrocarbon solvent in the presence of an amine catalyst, wherein the pentaerythritol has an average particle size of about 250 microns or less, wherein the amine catalyst is capable of forming an amine hydrochloride salt that is soluble in the hydrocarbon solvent, and wherein the reaction temperature is maintained at less than about 90° C. until the pentaerythritol has been consumed.

In a sixth embodiment of the present invention, the pentaerythritol, phosphorous trihalide, and a hydroxyl-containing compound are allowed to react together in a hydrocarbon solvent, wherein the pentaerythritol has an average particle size of about 250 microns or less, wherein the resultant reaction mixture has an acid number of less that about 2.

In a seventh embodiment of the present invention, the pentaerythritol, phosphorous trihalide, and a hydroxyl-containing compound are allowed to react together in a hydrocarbon solvent, wherein the pentaerythritol has an average particle size of about 250 microns or less, wherein the resultant reaction mixture has an acid number of less that about 1.

In an eighth embodiment of the present invention, the hydroxyl-containing compound is a phenol of the general formula:

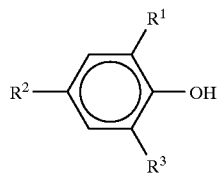

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl.

In a ninth embodiment of the present invention, the hydroxyl-containing compound is a phenol of the general formula:

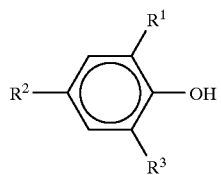

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with the proviso that at least one of $R^1$ and $R^2$ is t-butyl, t-amyl, t-hexyl, cyclohexyl, cumyl, t-pentyl, or t-octyl.

In an tenth embodiment of the present invention, the hydroxyl-containing compound is a phenol of the general formula:

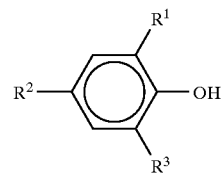

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with the proviso that at least one of $R^1$ and $R^2$ is t-butyl, t-amyl, t-hexyl, cyclohexyl, cumyl, t-pentyl, or t-octyl, and $R^3$ is hydrogen.

In a eleventh embodiment of the present invention, the hydroxyl-containing compound is 2,4-di-tertbutylphenol.

In a twelfth embodiment of the present invention, the organic spiro bis-phosphite made by the process is of the formula:

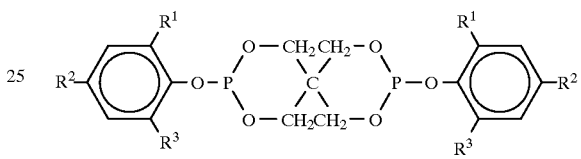

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl.

In an thirteen embodiment of the present invention, the organic spiro bis-phosphite made by the process is of the formula:

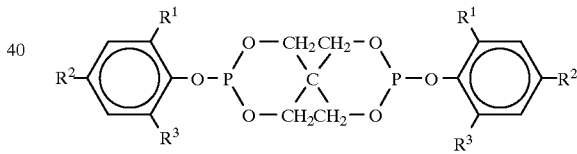

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with the proviso that at least one of $R^1$ and $R^2$ is t-butyl, t-amyl, t-hexyl, cyclohexyl, cumyl, t-pentyl, or t-octyl.

In a fourteenth embodiment of the present invention, the organic spiro bis-phosphite made by the process is of the formula:

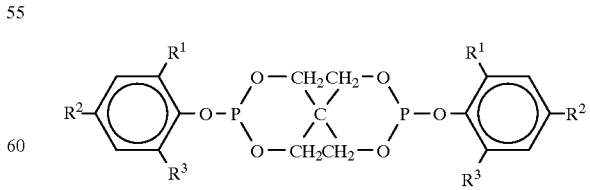

wherein each $R^1$ and $R^2$ is independently selected from the group consisting of methyl, ethyl, n-propyl, iso-propyl, n-butyl, t-butyl, t-amyl, t-hexyl, cyclohexyl, cumyl, t-pentyl, and t-octyl, and $R^3$ is hydrogen.

In a fifteenth embodiment of the present invention, the organic spiro bis-phosphite made by the process is of the formula:

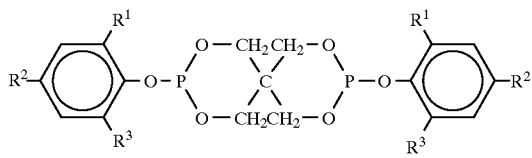

wherein each $R^1$ and $R^2$ is t-butyl and $R^3$ is hydrogen.

In a sixteenth embodiment of the present invention, the conversion in the process to the organic spiro bis-phosphites of the formula:

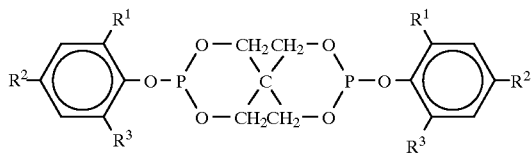

wherein each $R^1$ and $R^2$ is independently selected from the group consisting of methyl, ethyl, n-propyl, iso-propyl, n-butyl, t-butyl, t-amyl, t-hexyl, cyclohexyl, cumyl, t-pentyl, and t-octyl, and $R^3$ is hydrogen is at least about 50%.

These and other embodiments of the present invention will become apparent to those skilled in the art with the disclosure of the present invention.

DETAILED DESCRIPTION OF THE INVENTION

The present invention relates to processes to produce organic spiro bisphosphites is of the formula:

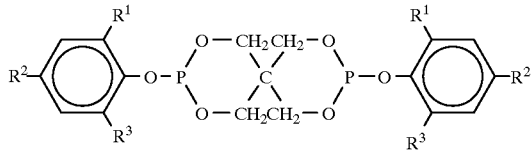

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl. In general, organic phosphites are typically produced by reacting a phosphorous trihalide, e.g., phosphorous trichloride, with hydroxyl-containing compounds wherein the halides are displaced on the phosphorous trihalide by the hydroxyl-containing compounds. The ease of substitution by the hydroxyl-containing compounds depends at least partly on the steric bulk of the hydroxyl-containing compounds. When the hydroxyl-containing compound has a low steric demand (i.e. the hydroxyl-containing compound is not a sterically hindered hydroxyl-containing compound), the displacement of the halides is somewhat statistical. However, as the steric demand of the hydroxyl-containing compound increases, increased selectivity may be obtained to achieve less substituted halophosphites. In displacement of the first two halides on the phosphorous trihalide, the reactions are generally facile and proceed to completion without the need for catalysis regardless of the steric limitations of the hydroxyl-containing compound.

In the displacement of the third halide moiety from the di-substituted phosphorus halide, the degree of conversion to the tri-substituted phosphite is adversely affected by steric considerations of both the di-substituted phosphorus halide and the hydroxyl-containing compound. Catalysts, including amines, are often employed in the art to increase the degree of conversion to the tri-substituted phosphite. Unfortunately, amine catalysts generally result in insoluble amine halide salt impurities in the desired spiro bis-phosphite compound and purification steps must be undertaken to remove the salt.

In one preferred embodiment of the present invention, the amine catalyst is selected such that the resultant amine halide salt is soluble in the reaction solvent. This avoids having to purify the desired end-product to remove the salt. The catalyst used may vary depending on the exact solvent utilized, however, useful catalysts include all those known in the art that remain soluble in the reaction mixture. Especially preferred amine catalysts include, for example, tri-(n-butyl) amine and tri-(iso-pentyl)amine. It should be clear, however, the other catalysts, especially catalysts that remain soluble in the reaction mixture, are also useful in the present process.

Elevating the reaction mixture is also known in the art to assist in driving the reaction towards completion. In the case of spiro bis-phosphites derived from pentaerythritol, elevating the temperature above about 80° C. leads to increases in the level of byproducts of the general formulas:

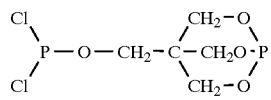

and

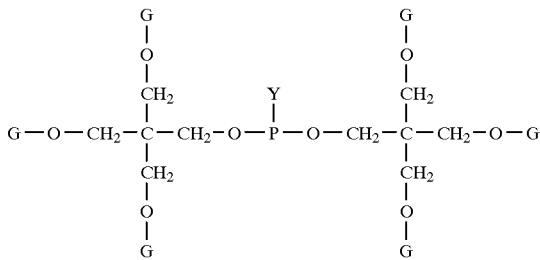

wherein Y is halogen or another good leaving group and each G can independently be a phosphorous or hydrogen increases as the temperature is increased beyond about 80° C. When G is a phosphorous, various polyphosphite compounds are possible. These byproducts and other similar by-products are difficult to remove from the desired Spiro bisphosphite compound and can have a negative affect on the stability of the desired spiro bisphosphite and accordingly are extremely undesirable.

It was quite surprising to discover that the use of finely ground pentaerythritol can readily drive the esterification reaction towards completion. In the present process, the pentaerythritol has a relatively poor solubility in the reaction media. Generally with organic phosphites, the displacement of the third halide is considerably slower than the displacement of the other halides, however, the displacement commonly proceeds to afford high conversions to the tris-substituted organo-substituted phosphite. In the case of pentaerythritol and sterically hindered phenols, the reaction is extremely sluggish and proceeds only to about 30% completion after more than 10 hours when neither vacuum nor catalyst are utilized. Surprisingly, under the same reaction conditions, use of finely ground pentaerythritol in the reaction mixture leads to dramatic increases in the rates of conversion as compared to the same or similar reaction conditions using pentaerythritol that has a larger average particle size. By finely ground is meant pentaerythritol having an average particle size of about 250 microns or less, preferably of about 150 microns or less, and most preferably of about 75 microns or less. The magnitude of the increase in the conversion is quite surprising when compared to a control that does not utilize finely ground pentaerythritol. It is also possible to use a combination of vacuum and catalyst with the finely ground pentaerythritol to achieve even higher and faster conversions. When vacuum is utilized, the vacuum should be at least about 10 inches of mercury, preferably of at least about 15 inches of mercury, and most preferably of at least about 25 inches of mercury. It should be clear, however, that in a preferred embodiment of the present invention, the esterification reaction is carried out in the presence of a catalyst that remains soluble in the reaction mixture.

The reaction between pentaerythritol, the hydroxyl-containing compound (e.g., the hindered phenol), and the phosphorous trihalide is quite exothermic but a temperature moderating effect is produced by the cooling effect of vigorous hydrogen halide evolution. The phosphorous trihalide is commonly $PCl_3$. The sequence of addition may vary between the addition of the ingredients, however, in a preferred embodiment, the finely ground pentaerythritol and the hydroxyl-containing compound are placed together in a solvent with any catalyst and the phosphorous trihalide is metered in such that the reaction mixture remains below about 80° C., preferably below about 50° C., and most preferably at about 40° C. Hence, by effective control of the addition of phosphorous trihalide, the reaction may be made self-regulating in the temperature range of between about 25° to 50° C. Control of reaction temperature helps to minimize the aforementioned by-products. A slight excess of stoichiometric amounts of phosphorous trihalide is commonly utilized.

It is important that the solvent be neutral to the reaction ingredients and by-products. Typical solvents include, for example, toluene, heptane, xylene, NORPAR, ISOPAR, methylene chloride, chloroform, and benzene. Judicious selection of the solvent allows for the desired product to be insoluble and filterable while the by-products, catalyst, and reaction intermediates remain soluble. Preferred solvents are toluene, heptane, or xylene, as well as mixtures of solvents. The amount of the solvent utilized can vary widely depending at least in part on the process capability of the equipment and an exact amount can be readily determined. Useful levels include, for example, on a weight to weight basis based on the amount of pentaerythritol to solvent from about 10:1 to about 1:10, preferably from about 1:1 to about 1:5.

After the addition of the phosphorous trihalide is competed, the reaction may be driven towards completion by gently raising the temperature of the reaction mixture to about 90° C. over about a 3 to 10 hour period. The utilized solvent may be at least partially removed, typically by application of a vacuum, to insure complete removal of the hydrogen halide by-product and to yield the desired product. The degree of completion of the reaction may be followed by standard techniques in this art, including, for example, by liquid or gas chromatography. Typical reaction times to substantial completion are up to about 24 hours. Preferably, the temperature and pressure conditions are selected to afford the maximum amount of product within a time period of about 8 to about 12 hours.

The final proportions of reactants are at least approximately stoichiometric. It is often desirable to work with at least a slight stoichiometric excess of one of the reactants to help drive the reaction as far to completion as possible. In a preferred embodiment of the present invention, the phosphorous trihalide is used as a relatively small excess of about 2 mole % based on the amount of the pentaerythritol. The high conversion rates obtained for the final bis-phosphite in the present process are especially unexpected when compared to the very long reaction times required when using a larger particle size pentaerythritol even with an excess of phosphorous trihalide as great as 10 mole %. The final product is commonly collected via filtration and is washed with additional solvent. The combined solvent can be recycled into another esterification reaction in order to maximize the utilization of the reactants.

The reaction product can be dissolved in an inert organic solvent and filtered to remove any solid materials. The solvent can be removed by flash distillation or another solvent removal technique or alternatively, the phosphite product can be isolated by crystallization or precipitation from an inert organic solvent. Typical inert organic solvents include hexane, heptane, octane, toluene, isopropyl alcohol, acetonitrile, and the like as well as various mixtures thereof. The phosphite product can also be purified using melt crystallization techniques or combinations of melt crystallization and solvent crystallization and/or precipitation.

When the phosphite stabilizer is isolated in crystalline form, the present invention contemplates that it may be utilized in solid amorphous form. The amorphous phosphite composition is formed by rapid cooling of melt of the phosphite. Such melt may be a mixture of the phosphite and polyamine which is rapidly cooled to form a solid amorphous phosphite composition. The amorphous nature of composition enhances the hydrolytic stability of the solid composition compared to crystalline composition containing the same constituents.

The phosphites made by the process of the present invention include all organic phosphites derived from pentaerithritol and hydroxyl-containing compound of the general formula:

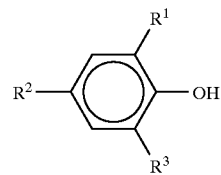

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl. Especially preferred phosphites, however, are sterically hindered spiro bis-phosphites wherein the hydroxyl-containing compound is a phenol of the general formula:

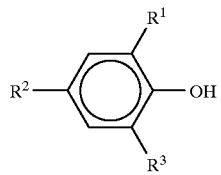

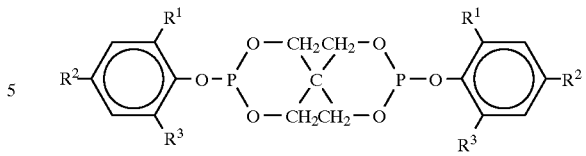

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with the proviso that at least one of $R^1$ and $R^2$ is t-butyl, t-amyl, t-hexyl, cyclohexyl, cumyl, t-pentyl, or t-octyl, and $R^3$ is hydrogen. In the practice of the present invention, as especially preferred organic spiro bis-phosphites is of the formula:

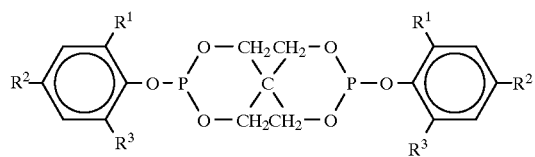

wherein each $R^1$ and $R^2$ is t-butyl and $R^3$ is hydrogen.

All patents cited by reference are incorporated herein by reference.

In order that those skilled in the art will be better able to practice the invention, the following examples are given by way of illustration and not by way of limitation.

EXAMPLES

General Procedure

A reaction vessel was charged with 2,4-di-t-butylphenol (173.3 g), pentaerythritol that had been ground to less that 200 mesh (54.4 g), tri(n-butyl)amine (0.38 g) with heptane (200 g) and was warmed to about 40° C. under an inert atmosphere. Phosphorus trichloride (111.6 g) was added to the reaction mixture with rapid stirring over a period of about two hours while maintaining the reaction mixture at about 40° C. The reaction was allowed to continue at 40° C. for an additional two hours. The temperature was increased to 50° C. and held for one hour, followed by increasing to 60° C. for one hour, followed by increasing to 70° C. for one hour and followed by increasing to 80° C. for one hour. After 6 hours since the completion of the addition of the $PCl_3$, the temperature was increased to about 92° C. and a vacuum of about 2.5 inches of mercury was applied to the reaction mixture. After about 2 to 3 hours, the vacuum was increased to about 12 inches while the temperature was decreased to about 80° C. The reaction was checked periodically for completion as determined by an acid number of less than 1 as measured by base titration. After completion, the temperature was decreased to about 60° C. and the vacuum was increased to about 21 inches for about 2 hours. The slurry was filtered hot and the wetcake was washed with additional heptane. A second reaction was charged with 2,4-di-t-butylphenol and pentaerythritol and 214 g. of filtrate from the above described reaction. The same procedure was followed for a second reaction. The degree of product conversion to the tri-substituted phosphite was measured by gas chromatography. The resultant phosphite had the formula:

wherein each $R^1$ and $R^2$ is t-butyl and $R^3$ is hydrogen and was 99.8% pure with an acid number of less than 0.2. The yield was 93% based upon the amount of pentaerythritol.

Control reaction

The general procedure was carried out as described above, however, the pentaerythritol had an average particle size of about 545 microns, a size that is typical for commercially available pentaerythritol. After about 30 hours reaction time, the same resultant phosphite was obtained with a yield of 64% based upon the amount of pentaerythritol and a purity of 99.8% with an acid number of 0.2. Increasing the reaction time or temperature resulted in a decrease in the purity of the desired phosphite.

The above examples demonstrate the unexpectedly high conversion and yield that can be obtained in a short reaction time with the use of pentaerythritol that had been finely ground in the process as described as compared to the same process utilizing pentaerythritol of a larger average particle size.

What is claimed:

1. A process to produce an organic spiro bis-phosphite, wherein said process comprises heating a reaction mixture containing pentaerythritol, phosphorous trihalide, and a hydroxyl-containing compound wherein the pentaerythritol has an average particle size of about 250 microns or less.

2. The process of claim 1, wherein the pentaerythritol has an average particle size of about 150 microns or less.

3. The process of claim 1, wherein the pentaerythritol, phosphorous trihalide, and the hydroxyl-containing compound are allowed to react together in a hydrocarbon solvent.

4. The process of claim 3, wherein the pentaerythritol, phosphorous trihalide, and the hydroxyl-containing compound are allowed to react together in a hydrocarbon solvent in the presence of a catalyst.

5. The process of claim 4, wherein the catalyst is an amine capable of forming an amine hydrochloride salt that is soluble in the hydrocarbon solvent.

6. The process of claim 1, wherein the pentaerythritol, phosphorous trihalide, and the hydroxyl-containing compound are allowed to react together in a hydrocarbon solvent, and wherein the reaction temperature is maintained at less than about 95° C.

7. The process of claim 5, wherein the reaction temperature is maintained at less than about 95° C.

8. The process of claim 3, wherein the resultant reaction mixture has an acid number of less than about 2.

9. The process of claim 8, wherein the resultant reaction mixture has an acid number of less than about 1.

10. The process of claim 1, wherein the hydroxyl-containing compound is a phenol of the general formula:

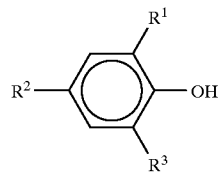

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl.

11. The process of claim 1, wherein the hydroxyl-containing compound is a phenol of the general formula:

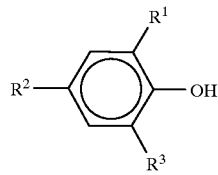

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with the proviso that at least one of $R^1$ and $R^2$ is t-butyl, t-amyl, t-hexyl, cyclohexyl, cumyl, t-pentyl, or t-octyl.

12. The process of claim 1, wherein the hydroxyl-containing compound is a phenol of the general formula:

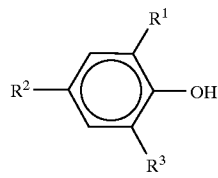

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with the proviso that at least one of $R^1$ and $R^2$ is t-butyl, t-amyl, t-hexyl, cyclohexyl, cumyl, t-pentyl, or t-octyl, and $R^3$ is hydrogen.

13. The process of claim 1, wherein the hydroxyl-containing compound is 2,4-di-tertbutylphenol.

14. The process of claim 1, wherein the organic spiro bis-phosphite made by the process is of the formula:

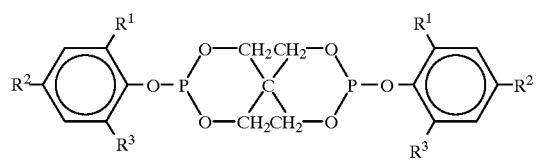

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl.

15. The process of claim 1, wherein the organic spiro bis-phosphite made by the process is of the formula:

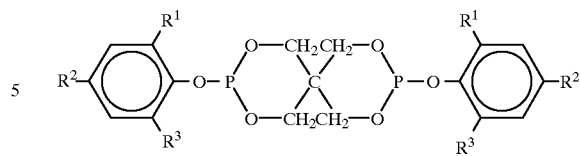

wherein each $R^1$, $R^2_1$ and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with the proviso that at least one of $R^1$ and $R^2$ is t-butyl, t-amyl, t-hexyl, cyclohexyl, cumyl, t-pentyl, or t-octyl.

16. The process of claim 1, wherein the organic spiro bis-phosphite made by the process is of the formula:

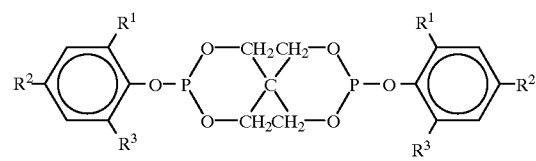

wherein each $R^1$ and $R^2$ is independently selected from the group consisting of methyl, ethyl, n-propyl, iso-propyl, n-butyl, t-butyl, t-amyl, t-hexyl, cyclohexyl, cumyl, t-pentyl, and t-octyl, and $R^3$ is hydrogen.

17. The process of claim 1, wherein the organic spiro bis-phosphite made by the process is of the formula:

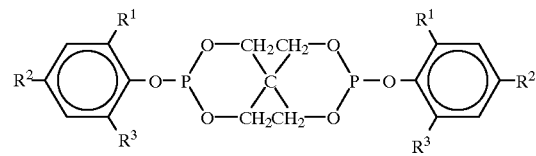

wherein each $R^1$ and $R^2$ is t-butyl and $R^3$ is hydrogen.

18. The process of claim 1, wherein the conversion in the process to the organic spiro bis-phosphites is at least about 70%.

19. A process to produce an organic spiro bis-phosphite of the formula

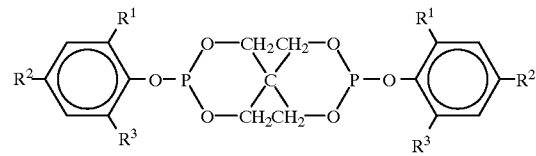

wherein $R^1$ and $R^2$ are each 2,4-di-tert-butyl and $R^3$ is hydrogen, wherein said process comprises heating a reaction mixture containing pentaerythritol wherein the pentaerythritol has an average particle size of about 250 microns or less, a phosphorous trihalide, a phenolic compound of the formula:

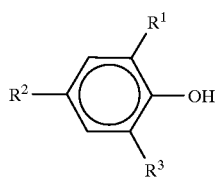

wherein each $R^1$ and $R^2$ is t-butyl and $R^3$ is hydrogen, a solvent selected from the group consisting of heptane, hexane, octane, xylene, toluene, and mixtures of the solvents containing at least one of the aforementioned, and a catalyst.

20. The process of claim 19, wherein the phosphorous trihalide is phosphorous trichloride.

21. The process of claim 19, wherein the pentaerythritol has an average particle size of about 150 microns or less.

22. The process of claim 19, wherein the catalyst is an amine capable of forming an amine hydrochloride salt that is soluble in the hydrocarbon solvent.

23. The process of claim 19, wherein a vacuum of at least about 10 inches of mercury is applied to the reaction mixture.

24. The process of claim 19, wherein the temperature of the reaction mixture is maintained between about 30° C. and about 95° C.

* * * * *